(12) United States Patent
Cassemeyer et al.

(10) Patent No.: US 8,075,548 B2
(45) Date of Patent: Dec. 13, 2011

(54) DEVICE FOR STORING AND ADMINISTERING ACTIVE INGREDIENTS, AND METHOD FOR ADMINISTERING ACTIVE INGREDIENTS BY MEANS OF SUCH DEVICE

(75) Inventors: Julia Cassemeyer, Reutlingen (DE); Sandra Kruse, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 12/452,446

(22) PCT Filed: Jun. 27, 2008

(86) PCT No.: PCT/EP2008/058227
§ 371 (c)(1),
(2), (4) Date: Mar. 9, 2010

(87) PCT Pub. No.: WO2009/003923
PCT Pub. Date: Jan. 8, 2009

(65) Prior Publication Data
US 2010/0168715 A1 Jul. 1, 2010

(30) Foreign Application Priority Data
Jul. 2, 2007 (DE) .......................... 10 2007 030 710

(51) Int. Cl.
*A61M 31/00* (2006.01)
*A61M 37/00* (2006.01)
*A61N 1/30* (2006.01)

(52) U.S. Cl. ............ 604/520; 604/89; 604/92; 604/518; 604/21; 604/82

(58) Field of Classification Search .................... 604/87, 604/82, 520, 20, 21, 501, 518, 500, 89, 92, 604/19, 48; 601/139
See application file for complete search history.

(56) References Cited

U.S. PATENT DOCUMENTS

| | | | |
|---|---|---|---|
| 3,964,482 A | 6/1976 | Gerstel et al. | |
| 4,687,481 A | 8/1987 | Nuwayser | |
| 6,334,856 B1 | 1/2002 | Allen et al. | |
| 6,611,707 B1 * | 8/2003 | Prausnitz et al. | 604/21 |
| 2006/0024358 A1 | 2/2006 | Santini, Jr. et al. | |

FOREIGN PATENT DOCUMENTS

| | | | |
|---|---|---|---|
| DE | 10 2006 028 782 | | 12/2007 |
| WO | WO 02/28471 | | 4/2002 |
| WO | WO 2005/056103 | | 6/2005 |
| WO | WO2006/015299 | * | 2/2006 |
| WO | WO 2006/015299 | | 2/2006 |
| WO | WO2006015299 | * | 2/2006 |

* cited by examiner

*Primary Examiner* — Kevin C Sirmons
*Assistant Examiner* — Bradley Thomas, Jr.
(74) *Attorney, Agent, or Firm* — Kenyon & Kenyon LLP

(57) ABSTRACT

In an apparatus for storing and administering active substances, at least one transfer mechanism is provided, and a first reservoir that contains an active substance in dissolved form is also provided, the active substance being administered by way of the transfer mechanism. A second reservoir having the active substance in solid form is additionally provided in the apparatus.

13 Claims, 1 Drawing Sheet

DEVICE FOR STORING AND ADMINISTERING ACTIVE INGREDIENTS, AND METHOD FOR ADMINISTERING ACTIVE INGREDIENTS BY MEANS OF SUCH DEVICE

BACKGROUND OF THE INVENTION

1. Field of the Invention

The present invention relates to a device and a method for storing and administering active substances, e.g., medical or biochemical active substances.

2. Description of Related Art

Many variants are known for administering medications of various forms, e.g. medical or biochemical active substances. In addition to the use of commonly known syringes, microneedles are also, for example, proposed as a transfer means for the active substance into a skin.

There are in principle several important criteria that must be taken into account in this context. Among the important criteria are the mechanical stability and biocompatibility of the microneedles, but also the capability of storing sufficient quantities of active substances and administering them via the microneedles. Structures such as cavities or depressions can be disposed for this purpose inside the microneedles in order to store active substances.

U.S. Pat. No. 6,334,856 B1, for example, describes microneedles that have reservoirs for the storage of active substances. The reservoir is preferably disposed under the needles on the substrate side and connected via internal ducts, such as holes, to the internal region of the microneedles, with the result that active substances can be guided out of the reservoir and delivered through microneedles to a body that is to be treated.

To allow even relatively large quantities of active substances to be stored reliably, German patent application DE 10 2006 028782.7 (not previously published and therefore not prior art) proposes to dispose microneedles inside a package that forms the reservoir. The reservoir contains a carrier medium in which the active substance is present in dissolved form. The microneedles are thus embedded in the carrier medium having the active substance, and are thereby supplied with the active substance. Storage of the active substance in dissolved form can lead to problems, however, when the solubility limit of the carrier medium is reached. When the solubility limit of the carrier medium is reached and exceeded, precipitation of the solution then occurs and the active substance settles in solid form in the reservoir. In solid form, however, the active substance cannot be administered through the microneedles. The above-described concept thus comes up against a natural limit to the quantity of active substance that can be absorbed.

BRIEF SUMMARY OF THE INVENTION

It is an object of the present invention to make available an apparatus and a method that make possible storage of larger quantities of active substance as compared with proposals from the existing art.

The present invention has the advantage of avoiding any exceedance of the solubility limit of the carrier medium. Oversaturation of the carrier medium is, advantageously, not reached. A relatively large quantity of active substance can consequently be stored, as compared with previously known approaches. Rapid and convenient administration can thereby be achieved, even with large and very large quantities of active substance.

At the same time, sterile storage of the transfer means continues to be ensured. The previously observed so-called leakage problem, in which active substances slowly emerge or evaporate from the reservoir in unintended fashion, is also avoided. The transfer means can thus also be safely transported.

DETAILED DESCRIPTION OF THE INVENTION

Figure 1:
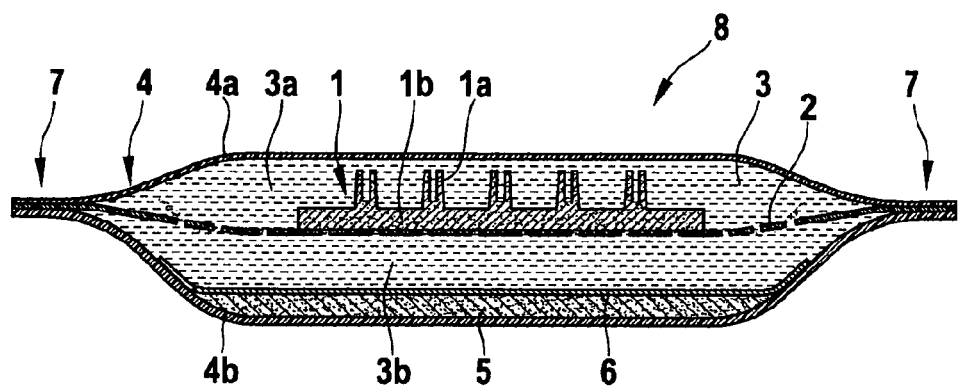
FIG. 1 shows a schematic sectioned depiction of an exemplifying embodiment of an apparatus for storing and transporting microneedles.

An apparatus 8 for storing and transporting microneedles 1a, 1b is proposed, providing firstly a first reservoir 3, 3a, 3b having a carrier medium, and at least one active substance dissolved therein for administration by way of at least one transfer means 1.

Such transfer means 1 can be, by way of example, a microneedle 1a, 1b. In the following exemplifying embodiments it is assumed that transfer means 1 is constituted by a microneedle 1a, 1b, other suitable transfer means 1 also being suitable in principle, instead of a microneedle 1a, 1b, for the inventive concept.

Microneedles 1a, 1b are advantageously disposed inside a package 4, 4a, 4b enclosing reservoir 3, 3a, 3b (FIG. 1). Because reservoir 3, 3a, 3b is not provided as a subregion of microneedles 1a, 1b, but instead is at least in part formed externally by a package 4, 4a, 4b, the reception of very large quantities of active substances is possible in practical fashion. At the same time, microneedles 1a, 1b are disposed inside package 4, 4a, 4b, i.e. microneedles 1a, 1b are provided in the midst of reservoir 3, 3a, 3b.

A very wide variety of embodiments of microneedles 1a, 1b themselves is known from the existing art. Advantageously, they are disposed in an array and have needle tips 1a on a substrate 1b. Microneedles 1a, 1b are made, as required, from a semiconductor material such as silicon, or else from plastic or metal.

In this exemplifying embodiment, microneedles 1a, 1b are mounted on a carrier 2 that is permeable to active substance. Carrier 2 can be implemented by way of a thin film having fine openings. Carrier 2 that is permeable to active substance extends through first reservoir 3, 3a, 3b, advantageously through the entire first reservoir 3, 3a, 3b. First reservoir 3, 3a, 3b is subdivided by carrier 2 into a first reservoir region 3a having microneedles 1a, 1b, and a second reservoir region 3b without microneedles 1a, 1b.

Package 4, 4a, 4b itself is formed by an elastic film 4a that can be pierced with microneedles 1a, 1b and by an outer layer 4b, which are connected to one another at their edge regions 7. In this case the upper region between film 4a and outer layer 4b, inside the connected edge regions 7, therefore forms first reservoir 3, 3a, 3b. Microneedles 1a, 1b are in turn carried by carrier 2 and are covered by elastic film 4a. The latter protects microneedles 1a, 1b during transport and storage, and moreover keeps microneedles 1a, 1b and the active substance sterile. Package 4, 4a, 4b, in particular film 4a, moreover prevents "leakage" or evaporation of the active substance.

Elastic film 4*a* and/or carrier 2 preferably have adhesive properties at least in their edge regions 7, thus making it possible to adhere film 4*a* and carrier 2 together by the exertion of pressure.

According to the present invention, a second reservoir 5 having the active substance in solid form is now provided in addition to first reservoir 3, 3*a*, 3*b*. Second reservoir 5 is preferably located adjacent to first reservoir 3; 3*a*, 3*b*, so that the first reservoir 3; 3*a*, 3*b* and second reservoir 5 adjoin one another.

A separating layer 6 can also advantageously be disposed between first reservoir 3; 3*a*, 3*b* and second reservoir 5. Separating layer 6 can be constituted by a porous elastic membrane, or by a film that is permeable to active substance.

In the exemplifying embodiment according to FIG. 1, second reservoir region 3*b* without microneedles 1*a*, 1*b* is disposed between first reservoir region 3*a* having microneedles 1*a*, 1*b* and second reservoir 5. First reservoir 3; 3*a*, 3*b* and second reservoir 5 themselves are surrounded by package 4; 4*a*, 4*b*. Second reservoir 5 is thus delimited on the front side, i.e. on the side facing toward microneedles 1*a*, 1*b*, by separating layer 6, and on the back side by outer layer 4*b* of package 4.

Because the additional active substance is present in solid form in a separate second reservoir 5, the solubility limit of the carrier medium in first reservoir 3; 3*a*, 3*b* is not exceeded. Driven by the concentration gradient, only as much active substance as permitted by its solubility limit diffuses into the carrier medium. The dissolved active substance can then diffuse via microneedles 1*a*, 1*b* into the skin.

Figure 2:
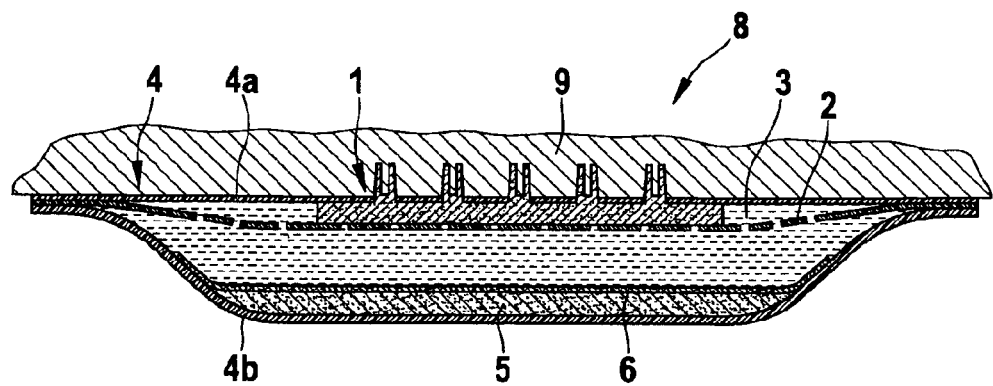
FIG. 2 shows an exemplifying embodiment of a method for administering active substances using an apparatus according to FIG. 1.

A method for administering active substances using the apparatus described above will now be explained with the aid of FIG. 2. The method encompasses the following steps:

- applying apparatus 8 onto a skin 9 that is to be treated;
- exerting a pressure onto apparatus 8, with the result that the at least one transfer means 1 pierces package 4; 4*a*, 4*b* and penetrates into skin 9;
- transporting the active substance out of first reservoir 3; 3*a*, 3*b* into skin 9 via transfer means 1.

Upon exertion of pressure onto apparatus 8, package 4; 4*a*, 4*b* ensures coverage of the remainder of the structure, and surrounds microneedles 1*a*, 1*b* laterally so that "leakage" is further minimized and the active substance emerges only through microneedles 1*a*, 1*b* and directly below the outermost skin layers. Active substance transport is ensured in this context by a process of diffusion out of the reservoir into the skin or body.

When a package 4*a*, 4*b* having an elastic film 4*a* and an outer layer 4*b* that are connected to one another at their edge regions 8 is used, and when microneedles 1*a*, 1*b* that are mounted on a carrier 2 that is permeable to active substance and extends through reservoir 3; 3*a*, 3*b* are used, upon exertion of pressure onto apparatus 8, carrier 2 is pressed against elastic film 4*a* and film 4*a* is pierced or penetrated by microneedles 1*a*, 1*b*. The active substance can now diffuse into skin 5 through microneedles 1*a*, 1*b*. As a result, the concentration of the active substance in the carrier medium drops, and new active substance can diffuse out of second reservoir 5 up to the solubility limit.

In a further embodiment, a film 4*a* and/or carrier 2 having adhesive properties at least in their edge regions 8 are used, with the result that upon the exertion of pressure onto apparatus 8, film 4*a* and carrier 2 adhere to one another and thus immobilize microneedles 1*a*, 1*b* and hold them in place. Microneedles 1*a*, 1*b* are thus immovably clamped in stable fashion between film 4*a* and carrier 2, and thus ensure controlled administration of the active substance.

It is noted in supplementary fashion that apparatus 8 as described above can be used as an active-substance patch. Apparatus 8 according to the present invention is suitable in general for use in the (bio)chemical, medical, and clinical sectors. Simple and also reliable utilization of the above-described apparatus 8 for the storage and administration of even very large quantities of active substances is made possible, without exceeding the solubility limit of the carrier medium.

What is claimed is:

1. An apparatus for storing and administering at least one active substance, comprising:

- a first reservoir containing a carrier medium and the at least one active substance dissolved in the carrier medium;
- at least one transfer mechanism for the dissolved active substance, the at least one transfer mechanism transferring the dissolved active substance to a surface external to the apparatus when activated;
- a second reservoir containing the active substance in solid form; and
- a transport structure configured to transport the solid active substance from the second reservoir to the first reservoir, wherein the transported solid active substance becomes dissolved in the carrier medium in the first reservoir;
- wherein:
  - the transport structure is a separating layer disposed between the first reservoir and the second reservoir;
  - a carrier structure permeable to the active substance extends across the first reservoir;
  - the transfer mechanism is mounted on the carrier structure; and
  - the first reservoir is divided into a first region having the transfer mechanism and a second region without the transfer mechanism.

2. The apparatus as recited in claim 1, wherein the first reservoir and the second reservoir adjoin one another.

3. The apparatus as recited in claim 1, wherein the separating layer is one of a porous elastic membrane or a film permeable to the active substance, the separating layer permitting transport of the active substance between the first and the second reservoirs when a concentration gradient exists between the first and the second reservoirs, the transport being permitted to an extent defined by a solubility limit of the active substance.

4. The apparatus as recited in claim 1, wherein a package surrounds the first and the second reservoir.

5. The apparatus as recited in claim 4, wherein the transfer mechanism for the active substance is a micro-needle.

6. The apparatus as recited in claim 5, wherein the package is formed from an elastic film forming an upper half of the package and an outer layer forming a lower half of the package, the elastic film configured to be pierced by the micro-needle when the package is compressed, and wherein the elastic film and the outer layer are connected to one another at their edge regions.

7. The apparatus as recited in claim 6, wherein the outer layer of the package seals off one side of the second reservoir.

8. A method for administering an active substance, comprising:

- providing an apparatus having:
  - a first reservoir containing a carrier medium and the active substance dissolved in the carrier medium;
  - at least one transfer mechanism for the active substance, wherein the transfer mechanism for the active substance is a micro-needle;
  - a second reservoir containing the active substance in solid form; and a package surrounds the first and the second reservoir;
applying the apparatus onto a target surface;
exerting a pressure on the apparatus to cause the micro-needle to pierce the package and penetrate into the target surface;
transporting the active substance out of the first reservoir into the target surface via the micro-needle; and
replacing an amount of active substance that is transported out of the first reservoir into the target surface by transporting the solid active substance from the second reservoir to the first reservoir, whereupon the transported solid active substance becomes dissolved in the carrier medium.

9. The apparatus as recited in claim 6, wherein:
a carrier structure permeable to the active substance extends across the first reservoir;
the transfer mechanism is mounted on the carrier structure;
the first reservoir is divided into a first region having the transfer mechanism and a second region without the transfer mechanism; and
the carrier structure adheres to the elastic film when the package is compressed, thereby immobilizing the transfer mechanism.

10. An apparatus for storing and administering at least one active substance, comprising:
a first reservoir containing a carrier medium and the at least one active substance dissolved in the carrier medium;
at least one transfer mechanism for the active substance, wherein the transfer mechanism is a micro-needle; and
a second reservoir containing the active substance in solid form;
wherein a carrier structure permeable to the active substance extends across the first reservoir, and wherein the transfer mechanism is mounted on the carrier structure, and wherein the first reservoir is divided into a first region having the transfer mechanism and a second region without the transfer mechanism;
wherein a package surrounds the first and second reservoirs, and wherein the package is formed from an elastic film forming an upper half of the package and an outer layer forming a lower half of the package, the elastic film configured to be pierced by the micro-needle, and wherein the elastic film and the outer layer are connected to one another at their edge regions.

11. An apparatus for storing and administering at least one active substance, comprising:
a first reservoir containing a carrier medium and the at least one active substance dissolved in the carrier medium;
at least one transfer mechanism for the dissolved active substance, the at least one transfer mechanism transferring the dissolved active substance to a surface external to the apparatus when activated;
a second reservoir containing the active substance in solid form; and
a transport structure configured to transport the solid active substance from the second reservoir to the first reservoir, wherein the transported solid active substance becomes dissolved in the carrier medium in the first reservoir;
wherein:
the first reservoir and the second reservoir adjoin one another;
the transport structure is a separating layer disposed between the first reservoir and the second reservoir;
a package surrounds the first and the second reservoir;
the transfer mechanism for the active substance is a micro-needle;
the package is formed from an elastic film forming an upper half of the package and an outer layer forming a lower half of the package;
the elastic film is configured to be pierced by the micro-needle when the package is compressed; and
the elastic film and the outer layer are connected to one another at their edge regions.

12. The apparatus as recited in claim 11, wherein the outer layer of the package seals off one side of the second reservoir.

13. The apparatus as recited in claim 11, wherein:
a carrier structure permeable to the active substance extends across the first reservoir;
the transfer mechanism is mounted on the carrier structure;
the first reservoir is divided into a first region having the transfer mechanism and a second region without the transfer mechanism; and
the carrier structure adheres to the elastic film when the package is compressed, thereby immobilizing the transfer mechanism.

* * * * *